United States Patent
Freyhof et al.

(10) Patent No.: US 6,200,429 B1
(45) Date of Patent: Mar. 13, 2001

(54) METHOD FOR TRIOXANE ISOLATION

(75) Inventors: Reinhard Freyhof, Frankenthal; Stefan Bitterlich, Dirmstein; Hugues Vandenmersch, Wachenheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/462,627
(22) PCT Filed: Jul. 2, 1998
(86) PCT No.: PCT/EP98/04094
§ 371 Date: Jan. 11, 2000
§ 102(e) Date: Jan. 11, 2000
(87) PCT Pub. No.: WO99/05137
PCT Pub. Date: Feb. 4, 1999

(30) Foreign Application Priority Data

Jul. 26, 1997 (DE) .............................. 197 32 291

(51) Int. Cl.[7] .............................. B01D 3/00; B01D 61/36; C07D 323/06
(52) U.S. Cl. .................................. 203/71; 159/DIG. 27; 159/DIG. 28; 203/78; 203/80; 210/664; 210/500.27; 210/500.38; 549/368
(58) Field of Search ................................. 203/14, 17, 53, 203/57, 54, 73, 71, 78, 79, 80; 159/DIG. 28, DIG. 27; 210/664, 500.21, 500.38, 500.27; 549/368

(56) References Cited

U.S. PATENT DOCUMENTS

| | | | |
|---|---|---|---|
| 4,125,540 | * 11/1978 | Sugio et al. | 549/368 |
| 4,952,319 | * 8/1990 | Yanaga et al. | 210/640 |
| 4,983,303 | * 1/1991 | Uragami | 210/640 |
| 5,061,349 | 10/1991 | Kupppenbender et al. | 549/368 |
| 5,523,419 | * 6/1996 | Arnold | 549/368 |
| 5,767,294 | * 6/1998 | Steele et al. | 549/368 |

FOREIGN PATENT DOCUMENTS 596 381   5/1994   (EP) .

OTHER PUBLICATIONS

Derwent JP 7/033762 A 95 02 03.

* cited by examiner

Primary Examiner—Virginia Manoharan
(74) Attorney, Agent, or Firm—Keil & Weinkauf

(57) ABSTRACT

A process for isolating trioxane from an aqueous mixture which includes trioxane, water and formaldehyde, including removing trioxane from the mixture by pervaporation, and subjecting the mixture enriched in trioxane (permeate) to rectification to give trioxane and an azeotropic mixture of trioxane, water and formaldehyde.

5 Claims, 1 Drawing Sheet

METHOD FOR TRIOXANE ISOLATION

The invention relates to a process for isolating trioxane from an aqueous mixture which consists essentially of trioxane, formaldehyde and water.

The preparation of trioxane results in an azeotropic mixture which consists essentially of trioxane, water and formaldehyde. Trioxane is isolated from this mixture by extraction with the aid of an entrainer, eg. chlorine-containing entrainers such as methylene chloride, or benzene. Further components of the mixture in minor amounts are, as a rule, formic acid, methylal and dimethoxydimethyl ether. The entrainer is recovered in a subsequent distillation and is returned to the extractive distillation. It is necessary for large amounts of entrainer to be employed in this process and to be recovered with high energy costs. Emissions which are inevitably produced require elaborate disposal because methylene chloride and benzene are categorized as hazardous substances.

EP-A 596 381 discloses a process for isolating trioxane by removal of water from the azeotropic mixture by pervaporation.

DESCRIPTION OF THE PREFERRED EMBODIMENT

Figure 1:
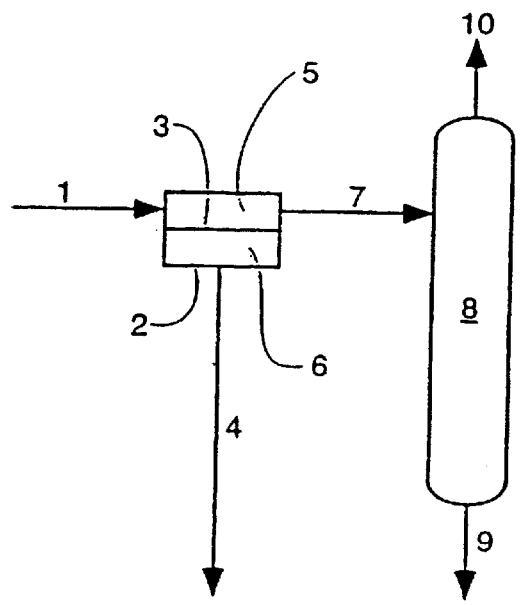
FIG. 1 is a showing of the conventional process.

The process of EP-A 596 381 may be briefly explained with reference to FIG. 1 as follows:

Water (line 4) is removed from an aqueous mixture (line 1) consisting of 65% by weight of trioxane, 27.5% by weight of water and 7.5% by weight of formaldehyde in a pervaporation unit 2 which contains a polyvinyl alcohol membrane 3 from Sulzer Chemtech GmbH-Membrantechnik, D-66540 Neunkirchen/Saar, at 90° C. The pressure on the retentate side 5 is 1 bar, and on the permeate side 6 is 50 mbar. Water is obtained as permeate, and a mixture of 84% by weight of trioxane, 10% by weight of formaldehyde and 6% by weight of water (line 7) is obtained as retentate. The retentate undergoes rectification in a column 8 under atmospheric pressure to give pure trioxane (bottom product, line 9) and an azeotropic mixture of trioxane, formaldehyde and water (overhead product, line 10).

This process has the disadvantage that it does not provide complete workup of the trioxane. It would not be worthwhile to recycle the column stream 10, for example before the pervaporation, because formaldehyde would accumulate.

It is an object of the present invention to provide a process for isolating trioxane from this azeotropic mixture to make isolation of trioxane as complete as possible.

We have found that this object is achieved by a process for isolating trioxane from an aqueous mixture which consists essentially of trioxane, water and formaldehyde, which comprises removing trioxane from the mixture by pervaporation, and subjecting the mixture enriched in trioxane (permeate) to rectification to give trioxane and an azeotropic mixture of trioxane, water and formaldehyde.

Preferred embodiments are evident from the dependent claims.

The novel process provides the advantages of substantially quantitative workup of the discharge from the reactor with recovery of the trioxane and formaldehyde which is as complete as possible. Furthermore, no other feedstocks are required.

Figure 2:
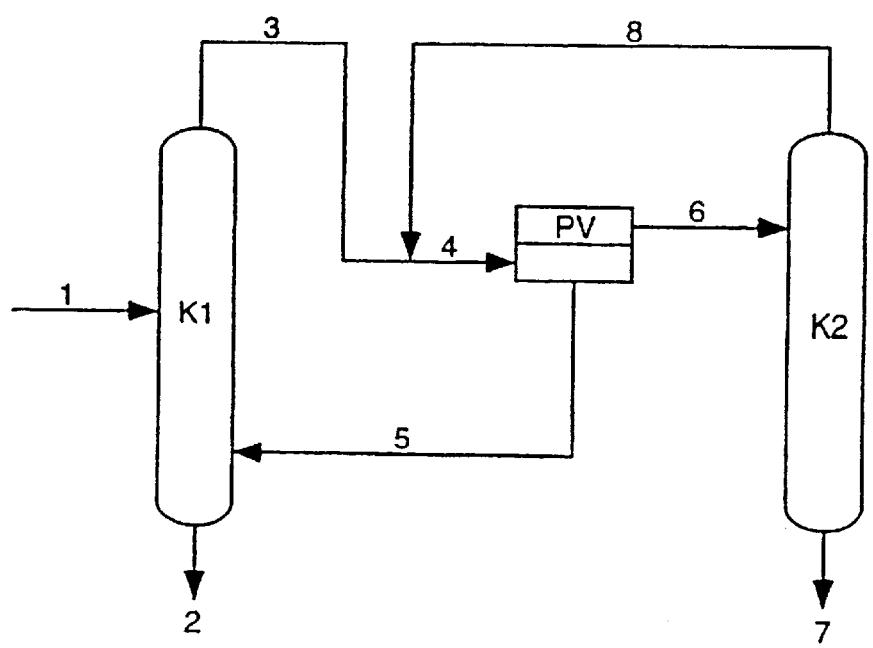
FIG. 2 is a showing of the process according to the present invention.

The novel process is explained with reference to FIG. 2 below.

Stream 1 represents the discharge from the reactor produced in the preparation of trioxane. As a rule, this consists essentially of 35–45% by weight of trioxane, 35–45% by weight of water and 15–30% by weight of formaldehyde.

Stream 1 is passed into a 1st rectification column K1 in which fractionation into 2 fractions takes place, with stream 2 containing a mixture of water and formaldehyde and stream 3 containing the azeotropic mixture.

The distillation preferably takes place in a rectification column K1 which may have up to 60 plates. The distillation takes place under atmospheric pressure as a rule.

Stream 2 is then recycled for formaldehyde concentration. The azeotropic mixture (stream 3) is transferred into a pervaporation unit (PV) which contains membranes suitable for organophilic pervaporation. The membranes used are normally pore-free polymer membranes in which the permeating component dissolves and diffuses through the membrane.

Examples of suitable membranes which may be mentioned are those made of polydimethylsiloxane and polyetheramide block copolymers. The polydimethylsiloxane membrane preferably contains a hydrophobic zeolite. The membrane thickness is preferably from 5 to 200 $\mu$m, preferably from 50 to 150 $\mu$m. Membranes of this type are commercially available under the proprietary name Pervap® 1070 from Sulzer Chemtech GmbH-Membrantechnik and PEBA 40 from GSE (Gesellschaft für Spezialfolienentwicklung).

The pervaporation is preferably carried out at from 70 to 120° C., preferably from 80 to 90° C. under from 1 to 3, preferably from 1 to 1.5, bar on the retentate side and from 10 to 150 mbar, preferably from 10 to 20 mbar, on the permeate side.

The trioxane-depleted stream 5 (retentate) is returned to the first distillation column K1, while the trioxane-enriched stream 6 (permeate) is passed into a second distillation column K2 in which rectification then takes place. This results in a trioxane fraction (stream 7) and an azeotropic mixture of the abovementioned constituents (stream 8). In turn, this mixture is recycled upstream of the pervaporation unit (stream 4). The trioxane fraction is the product and is passed (stream 7) into a reactor in which polyoxymethylenes are prepared from trioxane.

No additional components are required for the novel process. The discharge from the reactor is worked up very substantially quantitatively to recover/isolate formaldehyde and trioxane.

EXAMPLE

An aqueous mixture (stream 1) consisting of 40% by weight of trioxane, 40% by weight of water and 20% by weight of formaldehyde was distilled in a first column (K1, 25 stages) under atmospheric pressure to give a water/formaldehyde stream (stream 2) and an azeotropic mixture (stream 3).

Stream 3 was passed into the pervaporation unit which contained a polydimethylsiloxane membrane with a hydrophobic zeolite. The total thickness was 200 $\mu$m, and the supporting layer consisted of polyacrylonitrile. The thickness of the separating layer was 15–20 $\mu$m (Pervap® 1070 membrane from Sulzer Chemtech GmbH-Membrantechnik). The separation took place at 80° C. The pressure on the retentate side (5) was 1 bar and on the permeate side (6) was 10 mbar. The trioxane-enriched mixture (stream 6) was distilled in a second column (K2, 40 stages) under atmospheric pressure to give trioxane (stream 7) and once again an azeotropic mixture of trioxane, water and formaldehyde (stream 8). This mixture was recycled (stream 4) upstream of the pervaporation (PV).

The trioxane-depleted stream (stream 5) was returned to the first distillation column (K1). The bottom stream from this distillation column was passed on for formaldehyde concentration.

The amounts and concentrations of the various streams are compiled in the following table.

|  | Stream 1 | Stream 2 | Stream 3 | Stream 4 | Stream 5 | Stream 6 | Stream 7 | Stream 8 |
|---|---|---|---|---|---|---|---|---|
| Amount (kg/h) | 8000 | 4850 | 5892 | 8826 | 2742 | 6084 | 3150 | 2934 |
| Trioxane (% by wt.) | 40 | 1 | 58.1 | 61.4 | 9.9 | 84.6 | 99.95 | 68 |
| Water (% by wt.) | 40 | 66 | 30.6 | 29.2 | 65.8 | 12.7 | 0.05 | 26.3 |
| FA (% by wt.) | 20 | 33 | 11.3 | 9.5 | 24.3 | 2.7 | 0 | 5.7 |

In total, it was possible to recover 98.4% by weight of trioxane based on 3200 kg of trioxane employed ~100% by weight of formaldehyde based on 1600 kg of formaldehyde employed

We claim:

1. A process for isolating trioxane from an aqueous mixture which consists essentially of trioxane, water and formaldehyde, which comprises removing an azeotropic mixture consisting essentially of trioxane, water and formaldehyde from the aqueous mixture by a first rectification, removing trioxane from the azeotropic mixture by pervaporation, and subjecting the mixture enriched in trioxane as permeate to a second rectification to give trioxane and an azeotropic mixture of trioxane, water and formaldehyde.

2. A process as claimed in claim 1, wherein the pervaporation is carried out at from 70 to 120° C.

3. A process as claimed in claim 1, wherein the pervaporation is carried out under a pressure of from 1 to 3 bar on a retentate side and from 10 to 150 mbar on a permeate side.

4. A process as claimed in claim 1, wherein the pervaporation is carried out with a polydimethylsiloxane membrane or with a polyetheramide block copolymer membrane.

5. A process as claimed in claim 1, wherein the azeotropic mixture of trioxane, water and formaldehyde is returned after the second rectification to the pervaporation.

* * * * *